US 9,549,787 B2

United States Patent
Leiner et al.

(10) Patent No.: US 9,549,787 B2
(45) Date of Patent: Jan. 24, 2017

(54) MIXING AND APPLICATION CAPSULE FOR PRODUCING A DENTAL PREPARATION

(75) Inventors: Uwe Leiner, Midlum (DE); Manfred Thomas Plaumann, Cuxhaven (DE)

(73) Assignee: VOCO GMBH, Cuxhaven (DE)

(*) Notice: Subject to any disclaimer, the term of this patent is extended or adjusted under 35 U.S.C. 154(b) by 578 days.

(21) Appl. No.: 13/444,353

(22) Filed: Apr. 11, 2012

(65) Prior Publication Data
US 2012/0258422 A1 Oct. 11, 2012

(30) Foreign Application Priority Data

Apr. 11, 2011 (DE) .................. 20 2011 005 121 U

(51) Int. Cl.
A61C 5/04 (2006.01)
A61C 5/06 (2006.01)
B65D 81/32 (2006.01)

(52) U.S. Cl.
CPC ............... *A61C 5/064* (2013.01); *A61C 5/068* (2013.01); *B65D 81/3255* (2013.01)

(58) Field of Classification Search
CPC ......... A61C 5/062; A61C 5/066; A61C 5/064; A61C 5/068; A61C 9/0026; A61C 15/043; A61C 19/063
USPC ... 222/83, 136, 145.1, 145.5, 342, 378, 386, 222/386.5, 406, 407, 424.5, 527, 533, 222/534, 570; 206/63.5, 219, 221; 366/139, 176; 433/89, 90; 604/82, 83, 85, 604/87, 221, 222, 228, 229, 218, 311
See application file for complete search history.

(56) References Cited

U.S. PATENT DOCUMENTS

| | | | |
|---|---|---|---|
| 2,869,543 A | 8/1957 | Ratcliff | |
| 3,076,456 A | 2/1963 | Hunt | |
| 3,303,846 A | 2/1967 | Ogle | |
| 3,451,540 A * | 6/1969 | Kulischenko | A61C 5/066 206/220 |
| 3,557,787 A * | 1/1971 | Cohen | A61M 5/31596 604/90 |
| 3,595,439 A | 7/1971 | Newby et al. | |
| 3,724,460 A | 4/1973 | Gomez et al. | |
| 4,515,267 A | 5/1985 | Welsh | |
| 4,648,532 A * | 3/1987 | Green | A61C 5/064 206/222 |
| 4,674,661 A * | 6/1987 | Herold | A61C 5/062 222/386 |
| 4,941,751 A * | 7/1990 | Muhlbauer | A61C 5/064 206/217 |

(Continued)

FOREIGN PATENT DOCUMENTS

| | | |
|---|---|---|
| DE | 6948968 U | 5/1970 |
| DE | 285550 A5 | 10/1983 |

(Continued)

*Primary Examiner* — Matthew Nelson
(74) *Attorney, Agent, or Firm* — Duane Morris LLP; J. Rodman Steels, Jr.; Gregory M. Lefkowitz

(57) ABSTRACT

A mixing and application capsule for producing a dental preparation is described. The mixing and application capsule can have a capsule body with a mixing space for receiving a mixture component and for mixing the dental preparation from the mixture component and a fluid and with an outlet orifice for expelling the dental preparation, a cavity for receiving the fluid, a piston body that is movable in the capsule body, and delimits the mixing space in the capsule body and has a channel for conveying the fluid from the cavity into the mixing space. The piston body includes wholly or partly of two or a plurality of dissimilar materials, comprising at least one soft component and at least one hard component.

15 Claims, 11 Drawing Sheets

(56) References Cited

U.S. PATENT DOCUMENTS

| | | | |
|---|---|---|---|
| 5,172,807 A | 12/1992 | Dragan et al. | |
| 5,275,312 A * | 1/1994 | Labruzzo | B05B 11/0064 137/540 |
| 6,152,296 A * | 11/2000 | Shih | B65D 51/2835 206/222 |
| 6,386,872 B1 * | 5/2002 | Mukasa | A61C 5/066 206/219 |
| 7,311,195 B2 * | 12/2007 | Schmid | A61C 5/064 206/219 |
| 7,481,333 B2 * | 1/2009 | Goldberg | B05C 17/00506 222/1 |
| 7,748,567 B2 * | 7/2010 | Horner | A61C 5/062 222/135 |
| 2001/0053511 A1 * | 12/2001 | Aoyagi | A61C 5/062 433/90 |
| 2002/0098462 A1 * | 7/2002 | Kaneko | A61C 5/062 433/89 |
| 2002/0160333 A1 * | 10/2002 | Pierson | A61C 5/062 433/90 |
| 2004/0104133 A1 * | 6/2004 | Aoyagi | A61C 5/062 206/63.5 |
| 2006/0113201 A1 * | 6/2006 | Micic | B65D 81/3211 206/221 |
| 2007/0119868 A1 * | 5/2007 | Kraemer | B65D 83/0005 222/256 |
| 2007/0211563 A1 * | 9/2007 | De Vries | A61B 17/8825 366/139 |
| 2007/0255204 A1 * | 11/2007 | McLean | A61C 5/062 604/90 |
| 2009/0024082 A1 * | 1/2009 | McLean | A61C 5/062 604/85 |
| 2009/0236303 A1 * | 9/2009 | Lizerbram | B65D 47/243 215/227 |
| 2010/0261139 A1 * | 10/2010 | Leiner | A61C 5/064 433/90 |
| 2011/0166910 A1 * | 7/2011 | Marina | B65D 51/2807 705/7.29 |

FOREIGN PATENT DOCUMENTS

| | | |
|---|---|---|
| DE | 102009016862 A1 | 12/2010 |
| EP | 0783872 A2 | 7/1997 |
| WO | 0023002 | 4/2000 |

* cited by examiner

MIXING AND APPLICATION CAPSULE FOR PRODUCING A DENTAL PREPARATION

CROSS-REFERENCE TO RELATED APPLICATIONS

This application claims priority to German Patent Application No. DE 20 2011 005 121.8, filed Apr. 11, 2011, the entire content of which is incorporated herein by reference.

FIELD OF THE INVENTION

The present invention relates to a mixing and application capsule for producing a dental preparation.

BACKGROUND OF THE INVENTION

Mixing and application capsules are generally used for mixing two or a plurality of components, preferably a solid component and a fluid component, for example in order to produce a dental preparation, which is applied from the mixing and application capsule into a region within the oral cavity of a patient. In this way, for example glass ionomer cement is produced by mixing a powder component with a liquid component.

From the prior art, various devices and techniques are known that are devoted to accommodation of the solid component and of the fluid component within the mixing and application capsule, in order to achieve equally satisfactory mixing behavior and application behavior.

The liquid is for example accommodated in a film bag, which is opened by bursting. The film bag is then expressed, to force the liquid out of it and supply it to the pulverant component. This method has the drawback that during expressing, in particular with a bag that is very long relative to its diameter, the film forms folds, in which an indefinite residue of liquid remains. The result is that the dental preparation paste is mixed with insufficient liquid, so that it does not have the desired properties. Therefore either the size of the film bag and therefore the amount of liquid are restricted or else the dosage is inaccurate. The diameter of the film bag cannot as a rule be varied at will, as the capsule would need a correspondingly larger diameter. A capsule of large diameter is, however, disadvantageous during application in a patient's oral cavity. Moreover, the tongs used for expressing the mixing and application capsule are usually designed for small capsule diameters.

In one variant, a film bag is arranged laterally on or at the capsule body. Such a bag can therefore have a much larger diameter and amount of liquid. However, there is the disadvantage that a separate activating tool is required, for opening the film bag and bringing its contents in the capsule in contact with the powder (i.e. to activate the capsule). Also, proportionally more liquid is left behind in a bag with large diameter.

Another example of accommodation of a liquid in a mixing and application capsule for producing a dental preparation is described in U.S. Pat. No. 6,386,872 B1. A first and a second piston are arranged inside the capsule body, and a liquid is arranged in the space between them. The first piston delimits the mixing space inside the piston body, in which the pulverant component is arranged. The piston wall between mixing chamber and liquid space has a predetermined break point. If the second piston is pushed towards the mixing chamber, a projection on the second piston breaks through the predetermined break point of the wall of the first piston, so that the liquid flows into the mixing chamber, where it mixes with the pulverant component. After activation, for example by pressing the capsule by hand on a table top, the capsule must be clamped in a mixer, which mixes the powder and liquid by shaking, to form a paste.

Then the capsule is clamped in expressing tongs, with the aid of which both pistons are moved forward further. The paste is expelled through the cannula and for example fills a cavity of a tooth being treated.

The arrangement according to U.S. Pat. No. 6,386,872 B1 has the disadvantage that diffusion losses of the liquid occur and therefore the mixing and application capsule is not suitable for storage for a prolonged period. The seal between the first and second piston is a rubbing seal. If the seal is selected to be easy-running, so that a manual displacement of the second piston relative to the first piston is possible, there is inadequate sealing and the liquid can evaporate between the first and second piston. If the seal is selected to be so tight that evaporation of the liquid through the seal is avoided almost completely, the second piston can only be displaced relative to the first piston by applying a large force, which requires special tools and is no longer possible manually. Moreover, there is a similar problem of evaporation of the liquid for the seal between the first piston and the capsule body. The pulverant component in the mixing space is hygroscopic and therefore tends to take up moisture that penetrates through the seal between the first piston and the capsule body. This also impairs the long-term storage capability of the mixing and application capsule. In addition, the thin-walled region with the predetermined break point of the wall of the first piston can easily be penetrated by the liquid. The pulverant component can thus take up moisture from the liquid not only via the seal between first piston and capsule body, but also through the region with the predetermined break point of the wall of the first piston.

A mixing and application capsule that tackles and solves the problems of the rest of the prior art is known from DE 10 2009 016 862. The device known from DE 10 2009 016 862 is based on the double piston principle, wherein a first piston body is a double piston, and between the first piston body and the second piston body, a cavity is formed whose contents are forced out of the cavity through a channel when pressure is applied on the first piston body. If for example a fluid component is stored in the cavity and there is another mixture component, for example a powder component, in a mixing space connected to the cavity by the channel, motion of the double piston leads to mixing of the two components in the mixing space.

The manner of operation of the device known from DE 10 2009 016 862 is already satisfactory. However, in our own investigations of mixing and application capsules of the type known from DE 10 2009 016 862, in extreme test conditions sometimes the problem arose that small amounts of the mixture component from the mixing space get into the channel and pass through it towards the cavity. This has the effect that, in the extreme test conditions, occasionally with application of pressure and the concomitant forcing of the fluid component out of the cavity, mixing of the fluid component with the mixture component occurs in the mixing space even before the fluid component passes through the channel. This can theoretically lead to clogging of the channel, or—if the mixture component has set in other zones—to blocking of the movement of the first and/or second piston body, so that complete mixing of the two components and at worst also the complete expulsion of the dental preparation are made more difficult or are prevented.

Another problem that might sometimes arise with the known mixing and application capsule is that sometimes at the end of the phase of application of pressure and therefore at the end of expulsion of the dental preparation from the mixing space, liquid still flows out of the mixing and application capsule. This effect arises because to expel the paste, a relatively large force is applied, which is much higher than that required for activating the capsule, and thus for expelling the liquid. If activation is not carried out sufficiently completely, a small residue of liquid remains, which is then only discharged as a result of the large force during the application of pressure, i.e. during the operation of application.

SUMMARY OF THE INVENTION

Therefore the problem to be solved by the present invention was to overcome, to the greatest possible extent, the aforementioned drawbacks, occurring in extreme test conditions or theoretically.

The invention solves the aforementioned problem according to a first aspect, in the case of a mixing and application capsule for producing a dental preparation, wherein the mixing and application capsule has:

a capsule body with a mixing space for receiving a mixture component and for mixing the dental preparation from the mixture component and a fluid (42) and with an outlet orifice for discharging the dental preparation, a cavity for receiving the fluid, a piston body that is movable in the capsule body, and that delimits the mixing space in the capsule body and has a channel for conveying the fluid from the cavity into the mixing space, wherein the channel preferably has a closing means with one or a plurality of closing elements, which at zero pressure abut in such a way that the closing means is impervious to passage of mixture component into the channel, and which are arranged to release the channel on application of pressure on the cavity in the direction of the mixing space, wherein the piston body consists wholly or partly of two or a plurality of dissimilar materials, comprising at least one soft component and at least one hard component, and the closing elements of the closing means consist wholly or partly of the soft component.

The mixing and application capsule according to the first aspect of the invention preferably also has the features of a mixing and application capsule according to the second aspect of the invention (discussed below) and/or the third aspect of the invention (discussed below) and/or the fourth aspect of the invention (discussed below). All statements regarding preferred embodiments of the invention according to the second, third and fourth aspect of the invention also apply to this extent to the corresponding embodiments according to the first aspect of the invention.

The invention is based, according to the first aspect, on the finding that reliable closure of the channel against ingress of mixture component from the mixing space must be ensured mainly when no pressure is applied on the cavity. This is the case primarily during storage or transport of the mixing and application capsule. Therefore a closing element is preferably required that provides reliable closure at zero pressure, but which at the same time, on application of pressure, enables the channel for passage of fluid towards the mixing space. This is preferably realized according to the invention in that a closing means is formed on the channel, which consists of a soft component, which is simultaneously also part of the piston body, which consists of two or a plurality of different materials. According to the invention, the hard component and the soft component of the piston body are joined together mechanically. In this way, with a single component—the piston body—sufficient stability is provided by means of the hard component, and at the same time the closing means or its closing elements are provided in a suitable form by the soft component.

The joining of the two materials can be selected by a suitable combination of materials known by a person skilled in the art, in such a way that the two materials are joined solidly to one another. For pairs of materials that do not join together solidly, this can be compensated by constructing a non-positive or positive joint, for example a glued joint.

The mixture component preferably comprises a pulverulent material. Particularly preferably, the mixture component is a pulverulent material.

The pulverulent material preferably has an average particle size $d_{50}$ that is in a range from 1 µm through 100 µm. $d_{50}$ is to be understood as meaning the average particle size. By means of the design of the closing means according to the invention with closing elements made of soft component on a piston body, which consists wholly or partly of two or a plurality of dissimilar materials, comprising at least one soft component and at least one hard component, even very fine-grained mixture components can be stored in the mixing space, without their being able to pass through the channel towards the cavity with the fluid component. The good closing behavior of the closing elements formed from the soft component contributes decisively to this.

The mixture component is preferably contained in the mixing space of the capsule body.

According to a preferred embodiment, the closing elements are formed as flap valves or leaflet valves. In the closed state the closing elements preferably support one another, so that the sealing behavior of the closing element in the direction of the cavity is further improved. Modeled on a non-return valve, the flaps of the closing means can only fold in the direction of the mixing space, but not in the direction of the cavity. The opening and closing behavior of the closing elements is preferably modeled on the human or bovine heart valves. These combine the advantage of reliable closure with a maximum possible flow cross-section in the open state, which reduces the flow resistance and therefore the required pressing force when pressure is applied.

Preferably, for leaving the channel open, the closing elements are elastically deformable. As a result, when the closing elements move to an open position, a restoring force is produced, which provides automatic closure when the pressure is no longer applied. Through the elastic deformation behavior, the closing elements are also arranged for repeated opening and closing, for example if the application of pressure must be interrupted in the meantime.

The closing elements and the channel are preferably of one-piece design. Preferably the closing elements and the channel are joined together integrally. This is either ensured by the closing elements and the channel consisting of the same material, or of two different materials, wherein the closing elements consist of a soft component and the channel consists of a hard component. The closing elements and the channel are joined together preferably by means of gluing, welding, injection molding or clamping.

According to another preferred embodiment of the mixing and application capsule, the closing elements are designed to expose a slit-shaped, cross-shaped or star-shaped opening of the channel, on application of pressure. Preferably, a star-shaped opening is designed on the basis of an N-sided polygon, where N is preferably greater than or equal to 2. In preferred alternatives, the slit is either of linear design and/or follows a curve. A linear slit has better sealing behavior, because the slit area that has to be sealed is small in relation to the attainable opening. Conversely, with design of a slit along a curve, for example an omega or a circular arc, a larger opening cross-section can be achieved, which permits discharge of the fluid component into the mixing space with lower flow resistance. These last-mentioned section shapes are selected particularly preferably for a flat flap.

The same considerations can be applied to the design of the closing elements as flaps of a cross-shaped or star-shaped opening; the greater the number of flap-like closing elements that are formed (the higher the value of N for a star-shaped opening), the attainable opening cross-section is greater, but potentially the sealing force becomes lower owing to the increased sealing area. It is particularly preferable, in this connection, to arrange the closing elements in such a way that they support one another in the closed state, and preferably are arranged modeled on non-return valves.

In another preferred embodiment of the mixing and application capsule the closing element or the closing elements is/are adapted in order to release the channel on the application of pressure by means of crack formation, preferably in the material of the soft component or in the transition region between the materials of the soft component and the hard component.

The advantages according to the invention, which follow from the above considerations, are already obtained with a mixing and application capsule with just a single piston body. However, a mixing and application capsule according to one of the aforementioned preferred embodiments, with a second piston body movable in the capsule body relative to the first piston body that has the cavity for receiving the fluid, is particularly preferred.

Said flap or leaflet valve can moreover be positioned at the outlet orifice in the transition to the mixing cannula. The elasticity of the corresponding closing elements (flap wings) must however be higher at this point, to prevent penetration of the powder in the intended flow direction during storage and transport. As already described, for application of the prepared paste, a large force is available, owing to the use of a mechanical applicator/application tongs. This is preferably utilized so that the paste overcomes the comparatively high closing force of a flap valve positioned at the transition to the application cannula. A capsule with such a flap valve in the transition to the application cannula does not require any additional closing elements such as rotating or swiveling closures. It should be noted, however, that although a fixed cannula makes the cannula opening operation superfluous, during activation, i.e. when the piston is pushed in by pressing on a table top, it can be a hindrance.

Preferably the first piston body has a projection, and the cavity of the second piston body is designed to receive the projection of the first piston body.

The invention solves the problem on which it is based according to a second aspect with a mixing and application capsule for producing a dental preparation, wherein the mixing and application capsule has:

a capsule body with a mixing space for receiving a mixture component and for mixing the dental preparation from the mixture component and a fluid and with an outlet orifice for discharging the dental preparation, a cavity for receiving the fluid, a piston body that is movable in the capsule body, which delimits the mixing space in the capsule body and which has a channel for conveying the fluid from the cavity into the mixing space and a projection, wherein the cavity is designed to receive the projection of the first piston body, wherein the piston body consists wholly or partly of two or a plurality of dissimilar materials, comprising at least one soft component and at least one hard component, wherein the projection is formed on the piston body in such a way that the piston body has a structure with substantially constant wall thickness, preferably has a wall thickness in the range from 0.3 mm through 3 mm, and wherein the structure consists of the hard component.

The mixing and application capsule according to the second aspect of the invention preferably also has the features of a mixing and application capsule according to the first aspect and/or the third aspect of the invention (discussed below) and/or the fourth aspect of the invention (discussed below). All statements regarding preferred embodiments of the invention according to the first, third and fourth aspect of the invention also apply to this extent to the corresponding embodiments according to the second aspect of the invention.

This second aspect of the invention is based on the finding that the so-called after-discharge of liquid from the capsule is due to an incorrect mixing ratio or an incorrect manner of expulsion of fluid from the cavity into the mixing space. It has been found that through the application of pressure, which takes place when a high pressing force is applied, fluid is not delivered, as intended, completely and immediately through the channel and into the mixing space, but is also diverted into dead spaces that have formed between the channel and the cavity. The dead spaces form because during production of the piston body, dimensional distortion occurs; because the piston body must be able to withstand the high pressing force that has to be applied, in known devices it is made substantially as a massive component. Owing to the large numbers in which these hollow parts are produced, it has become unavoidable for technical reasons to cast the known hollow part as a massive component. During solidification, as is known, as a result of shrinkage of the material, dimensional distortion occurs at points with varying wall thickness, the effect being greater the larger the local wall thickness. Owing to this dimensional distortion, dead spaces form, in which fluid remains when pressure is applied. Because fluid is not expelled completely, either the mixture ratio is incorrect, or the fluid is only discharged at the end of the pressing operation, when all of the mixture component has already been expelled from the mixing space. It was found, surprisingly, that the mechanical stability of the piston body, which is necessary for withstanding the pressing force during the application of pressure, is also ensured by a structure with substantially constant wall thickness, wherein the structure consists of the hard component. Because substantially no wall thickness variations of the hard component are to be expected according to the solution according to the invention and therefore are avoided, the shrinkage of the material during solidification of the hard component of the piston body also does not lead to a varying extent of dimensional distortion and therefore to the formation of dead spaces. Therefore less liquid or even no liquid is now retained, and the application behavior of the mixing and application capsule is improved overall.

Preferably, one or a plurality of cavities are formed in the structure, which are filled wholly or partly with the soft component. By means of the soft component, in a second processing step, the structure can be filled at the desired regions in the cavities, so that the mechanical stability of the piston body is further improved, without having to accept local dimensional distortion as a result of shrinkage. The shrinkage that also occurs with the soft component is on the one hand less pronounced, because a large part of the volume is already occupied by the hard component, and on the other hand it would not be relevant, as it occurs in a region that does not play any role for the function of the component.

Preferably, the mixing and application capsule according to the second aspect of the invention has a second piston body that is movable in the capsule body relative to the first piston body, and has the cavity for receiving the fluid.

The invention solves the problem on which it is based according to a third aspect with a mixing and application capsule for production of a dental apparatus, wherein the mixing and application capsule has:

a capsule body with a mixing space for receiving a mixture component and for mixing the dental preparation from the mixture component and a fluid and with an outlet orifice for discharging the dental preparation, a cavity for receiving the fluid, a first piston body that is movable in the capsule body, and which delimits the mixing space in the capsule body, and has a channel for conveying the fluid from the cavity into the mixing space, a second piston body that is movable in the capsule body relative to the first piston body, and which has the cavity for receiving the fluid and a projection, wherein the channel is designed to receive the projection of the second piston body, and, wherein the projection and the channel are adapted to one another in such a way that with the projection and the channel bearing on one another, one or a plurality of flow channels remain.

The mixing and application capsule according to the third aspect of the invention preferably also has the features of a mixing and application capsule according to the first aspect and/or the second aspect of the invention and/or the fourth aspect of the invention (discussed below). All statements regarding preferred embodiments of the invention according to the first, second and fourth aspect of the invention also apply to this extent to the corresponding embodiments according to the third aspect of the invention.

According to this third aspect, the invention makes use of the finding that the so-called after-discharge of liquid also occurs because in known mixing and application capsules the projection that is received in the channel of the first piston body closes this completely in a late stage of the application of pressure, which hampers or prevents further expulsion of liquid. According to the invention, however, the cavity at first becomes smaller and smaller, and the projection penetrates further and further into the channel, until the projection and the channel bear against one another. In this state, liquid transport is still possible via the remaining flow channels. Preferably the projection and the channel each have one or a plurality of bearing surfaces, which close together with a fluid-tight seal when the projection and the channel bear against one another.

More preferably, in the one or a plurality of bearing surfaces of the projection, depressions are formed, with walls that define one or a plurality of flow channels for fluid transport.

Alternatively or additionally, in the one or a plurality of bearing surfaces of the channel, depressions are formed, with walls that define one or a plurality of flow channels for fluid transport.

The walls are preferably deformable in such a way that the flow channels, on application of a pressing force, are wholly or partly sealable in the bearing position on the projection and/or the channel. The walls are preferably deformable elastically or plastically. The advantage of this embodiment is that towards the end of the application of pressure, when the projection has already been brought up against the channel, through deformation of the channel and/or of the projection even the remaining flow channels are still sealable and therefore even the last residue of liquid can be expelled from the cavity into the mixing space.

The mixing and application capsule according to the third aspect of the present invention is therefore advantageously modified so that the first piston body consists wholly or partly of two or a plurality of dissimilar materials, comprising at least one soft component and one hard component, and the first piston body has, on its circumferential surface, a ring seal that consists wholly or partly of the soft component.

The ring seal is preferably designed so that it projects into the second piston body, thus providing improved sealing against the penetration of the fluid component. At the same time, the sliding behavior of this seal is greatly improved compared to the sliding behavior of the hard component, because the flexibility of the soft component advantageously improves reliable liquid-tight sealing, without requiring a high pressing force.

The ring seal ensures that the fluid component is propelled exclusively through the channel into the mixing space and does not get into any annular space along the circumferential surface of the first piston body.

Preferably the first piston body has a projection, wherein the cavity that is formed in the second piston body is designed to receive the projection of the first piston body.

According to a preferred embodiment of the present invention, the cavity is sealed by a separating layer, preferably a separating film, wherein the projection of the first piston body and/or the projection of the second piston body are arranged to penetrate the separating layer, when the first piston body and the second piston body are moved relative to one another.

Preferably the projection of the second piston body has, in sections or completely, a diameter that exceeds the diameter of the channel, so that when the projection enters the channel, starting from a certain depth of penetration, preferably in the range from 5 through 20 mm, the outside surface of the projection and the inside surface of the channel bear on one another fluid-tight.

Preferably the projection of the second piston body is substantially of conical form. More preferably, the channel has a, preferably conically, enlarged cross-section in the direction of the cavity. Particularly preferably, the projection of the second piston body is conical and the channel is of conically enlarged form. The interaction of these two geometrical shapes means that the projection can penetrate as far as possible into the channel, without the pressing force owing to the surface pressure that is to be applied between the projection and the channel becoming inadmissibly high.

In a preferred embodiment of the mixing and application capsule according to the invention, the projection of the first piston body has a cutting edge for cutting into the separating layer, wherein the cutting edge is arranged along the circumference of the projection of the first piston body, and wherein the ring seal is arranged proximally to the cutting edge, preferably at a distance of 0.5 mm through 5 mm. The smaller the distance between the seal and the cutting edge, the less liquid will be displaced overall into the annular space forming between the cutting edge and the seal, once the application of pressure begins.

The present invention solves the problem on which it is based according to a fourth aspect with a mixing and application capsule for production of a dental apparatus, mixing and application capsule for producing a dental preparation, wherein the mixing and application capsule has:

a capsule body with a mixing space for receiving a mixture component and for mixing the dental preparation from the mixture component and a fluid and with an outlet orifice for discharging the dental preparation, a cavity for receiving the fluid, a first piston body, movable in the capsule body, which delimits the mixing space in the capsule body, and has a channel for conveying the fluid from the cavity into the mixing space, and a second piston body, movable in the capsule body relative to the first piston body, which has the cavity for receiving the fluid, wherein the first piston body and/or the second piston body consist wholly or partly of two or a plurality of dissimilar materials, comprising at least one soft component and at least one hard component.

The mixing and application capsule according to the fourth aspect of the invention preferably also has the features of a mixing and application capsule according to the first aspect and/or the second aspect of the invention and/or the third aspect of the invention. All statements regarding preferred embodiments of the invention according to the first, second and third aspect of the invention also apply to this extent to the corresponding embodiments according to the fourth aspect of the invention.

Preferably the outlet orifice is arranged in a cannula, which is received on one end of the capsule body and can rotate or swivel by means of a hinged joint, wherein the cannula is secured in a recess on the capsule body by means of a snap-in connection, and wherein the direction in which the cannula is snapped-in is angled to the direction of discharge of the dental preparation. Preferably the direction in which the cannula is snapped-in is angled at an angle of 90° to the direction of discharge of the dental preparation.

Particularly preferably, the direction in which the cannula is snapped-in is angled at an angle of 45° to the direction of discharge of the dental preparation. The advantage of the angled arrangement of the direction of snapping-in of the cannula is that in this way the cannula can only be forced out of the snapped-in position with difficulty, or even not at all, by the application of pressure. The particularly preferred arrangement at a 45° angle additionally offers the advantage that the cannula, which can preferably be brought from a closed position to an open position by means of the hinged joint, in the open position can only be levered out of the snapped-in position with difficulty, when the cannula is pressed laterally on a surface.

According to another preferred embodiment of the mixing and application capsule according to the invention, the projection of the first piston body has a cutting edge for cutting into the separating layer, wherein the cutting edge is arranged along the circumference of the projection, and consists intermittently of the soft component and the hard component along the circumference. Preferably the cutting edge consists of soft component in four regions that are spaced angularly apart by 90° respectively. The advantage of the intermittent arrangement of regions of soft component and hard component along the periphery of the cutting edge is that owing to the local deformation of the soft component, stress concentrations are produced in the separating layer, which lead to accelerated tearing and parting of the separating layer.

According to another preferred embodiment of the mixing and application capsule according to the invention, the second piston body has, on an end opposite to the cavity, an overhang, preferably with rounded edges. The overhang makes it easier on the one hand for the user to apply a pressing force on the second piston body. On the other hand the overhang has, along its outer periphery, an edge that serves as visible indicator of how deep the second piston body has already penetrated into the capsule body and therefore of how much fluid has already been forced into the mixing space. Optionally, a scale is fitted on the outer circumferential surface of the second piston body to facilitate reading.

Preferably the material of the soft component comprises a thermoplastic elastomer (TPE), and the material of the hard component comprises polypropylene (PP). More preferably, the material of the soft component comprises silicone, and the material of the hard component comprises a polyester, preferably polybutylene terephthalate (PBT). Particularly preferably, the closing elements of the closing means are made of soft component. These material combinations have the advantage in each case that the soft component and the hard component adhere to one another, giving better sealing against the mixture component.

Alternatively or additionally, the material of the soft component comprises a thermoplastic elastomer (TPE) and the material of the hard component comprises polyoxymethylene (POM). More preferably, the material of the soft component comprises polyethylene and the material of the hard component comprises polypropylene. Moreover, both high-density polyethylene (HDPE) or low-density polyethylene (LDPE) can be used in conjunction with polypropylene. Particularly preferably, the closing elements of the closing means are made of soft component. These material combinations are considered to have the advantage that the soft component and the hard component do not adhere to one another, so that opening of the closing elements is facilitated. Alternatively, the combination of LDPE as soft component and HDPE as hard component is also envisaged, which make a firm joint with one another.

The aforementioned material combinations are selected in such a way that they can be used for manufacture by 2C injection molding.

Preferably the materials of the second piston body and of the separating layer are matched to one another. The second piston body preferably consists of high-density polyethylene, and the separating layer preferably consists of polyethylene. On the one hand this permits welding-on of the separating layer onto the second piston body. On the other hand polyethylene has improved diffusion impermeability against the evaporation of fluid from the cavity, in particular compared to polypropylene, which is used in known mixing and application capsules.

Other advantageous pairs of materials and the use of multilayer composites for pistons and/or separating layer with or without metallic or barrier layers are known by a person skilled in the art.

It has already been mentioned that the mixing and application capsule according to one of the aspects of the invention preferably also has the features of a mixing and application capsule according to one or more of the other aspects of the invention. All statements regarding preferred embodiments of the invention according to one of the aspects of the invention also apply to this extent to the corresponding embodiments according to the other aspects of the invention.

The invention therefore relates, in preferred embodiments, to a mixing and application capsule for producing a dental preparation, wherein the mixing and application capsule has:

a capsule body with a mixing space for receiving a mixture component and for mixing the dental preparation from the mixture component and a fluid and with an outlet orifice for discharging the dental preparation, a cavity for receiving the fluid, a piston body that is movable in the capsule body, and delimits the mixing space in the capsule body and has a channel for conveying the fluid from the cavity into the mixing space, wherein (first aspect of the invention) the channel has a closing means with one or a plurality of closing elements, which at zero pressure abut in such a way that the closing means is impervious to passage of mixture component into the channel, and which are arranged to release the channel on application of pressure on the cavity in the direction of the mixing space, wherein the piston body consists wholly or partly of two or a plurality of dissimilar materials, comprising at least one soft component and at least one hard component, and the closing elements of the closing means consist wholly or partly of the soft component, and/or wherein preferably (second aspect of the invention) the piston body has a projection, wherein the cavity is designed to receive the projection of the first piston body, wherein the piston body consists wholly or partly of two or a plurality of dissimilar materials, comprising at least one soft component and at least one hard component, wherein the projection is formed on the piston body in such a way that the piston body has a structure with substantially constant wall thickness, preferably has a wall thickness in the range from 0.3 mm through 3 mm, and wherein the structure consists of the hard component, and/or wherein preferably (third aspect of the invention) the mixing and application capsule has a second piston body that is movable in the capsule body relative to the first piston body, which has the cavity for receiving the fluid and a projection, wherein the channel is designed to receive the projection of the second piston body, and wherein the projection and the channel are adapted to one another in such a way that in a position with the projection and the channel bearing on one another, one or a plurality of flow channels remain, and/or wherein preferably (fourth aspect of the invention) the mixing and application capsule has a second piston body that is movable in the capsule body relative to the first piston body, and has the cavity for receiving the fluid, wherein the first piston body and/or the second piston body and/or the capsule body consist wholly or partly of two or a plurality of dissimilar materials, comprising at least one soft component and at least one hard component.

With respect to preferred embodiments of said mixing and application capsule, reference is to be made to the above account concerning the aspects of the present invention, which apply correspondingly, and to the examples given below.

The exemplary embodiments relate to mixing and application capsules that satisfy all aspects of the invention simultaneously. A person skilled in the art can, by omitting individual features, which correspond to individual aspects, generate further exemplary embodiments that satisfy a reduced number of aspects. It will be understood that the features of the exemplary embodiments that relate to different aspects (of the total of four aspects according to the invention) are relevant both when viewed together and independently of one another.

BRIEF DESCRIPTION OF THE DRAWINGS

In the following, the invention is explained in more detail with some exemplary embodiments and referring to the accompanying drawings, showing.

DETAILED DESCRIPTION

Figure 1A:
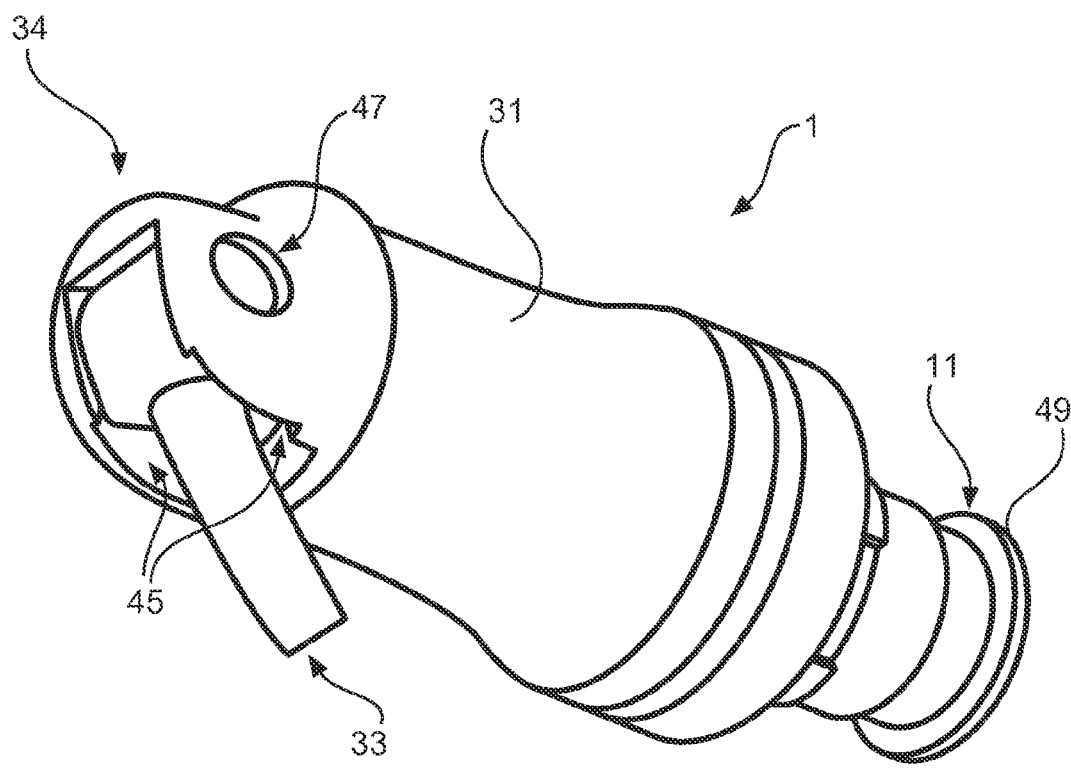
FIG. 1a is a three-dimensional representation of a mixing and application capsule of a first exemplary embodiment according to the first through fourth aspect of the invention.
Figure 1B:
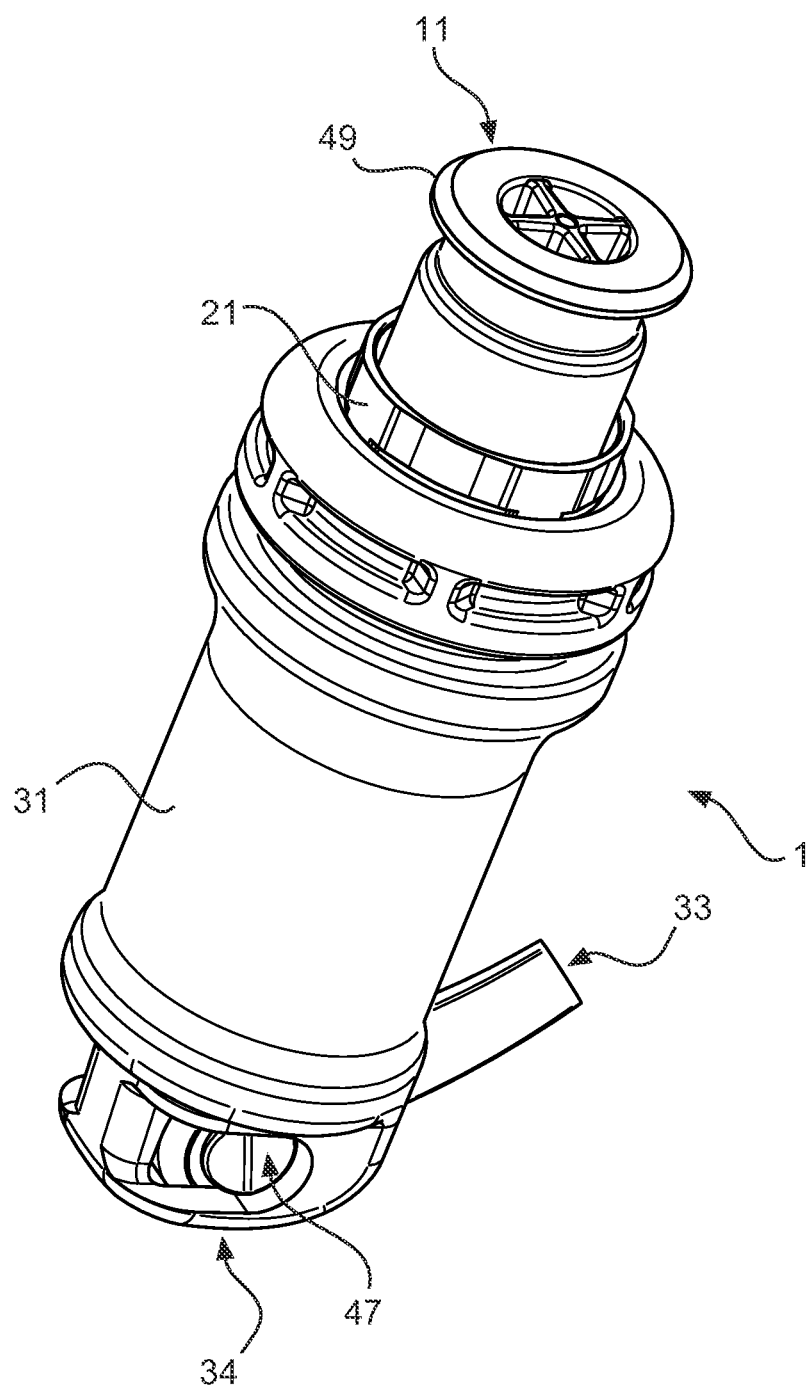
FIG. 1b is another three-dimensional representation of a mixing and application capsule of the mixing and application capsule of the first exemplary embodiment according to the first through fourth aspect of the invention.

FIGS. 1a and 1b show firstly an exterior view of a mixing and application capsule 1 according to the invention, called capsule 1 hereinafter. Capsule 1 has a capsule body 31. A first piston body 11 (see FIGS. 1a, 2) and a second piston body 21 are arranged inside the capsule body 1. The second piston body 21 extends partly outside of the capsule body 31. An overhang 49 is formed on the projecting end of the second piston body 21.

FIG. 1a, left, shows at one end of the capsule 1, which is arranged opposite the second piston body 21, a cannula 33 arranged with an outlet. The outlet is designed for application of the dental preparation within the oral region of a patient. The cannula can be moved to and fro between a closed position and an open position. The cannula is shown in the closed presentation in FIG. 1a. In this position, the outlet is not in fluid-conveying communication with the interior of the capsule body 31. The cannula 33 is held in a snap-in connection by two flanks 45 and is mounted rotatably therein by means of a seating 47. Further details of the cannula 33 can be seen in FIG. 12.

Liquid piston 21 has, in its interior, a projection in the form of a pin 25. The projection 25 corresponds in form and/or volume substantially to a channel 19, formed as a through-channel, of the punching piston 11. The channel 19 of the punching piston 11 is of conical shape in the embodiment in FIG. 4, to receive the pin 22. Other cross-sections, e.g. pyramid-shaped, cylindrical or star-shaped are also possible.

FIG. 1b shows the capsule 1 from a different viewing angle than the capsule 1 according to the first exemplary embodiment in FIG. 1a. Identical and similar parts are given the same reference symbols in FIG. 1b. To that extent, reference is made to the above description for FIG. 1a in its entirety.

Figure 2:
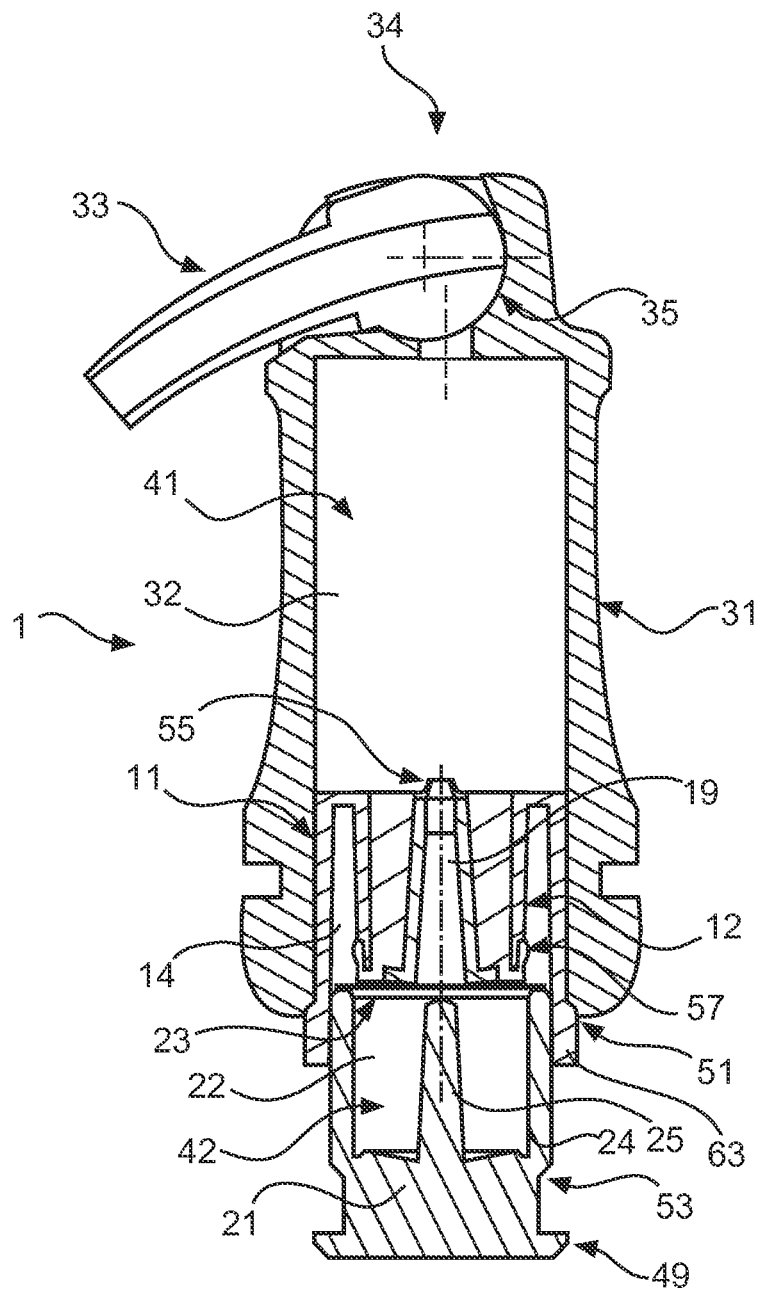
FIG. 2 is a cross-sectional view of the mixing and application capsule from FIG. 1a and 1b in a first operating position.
Figure 3:
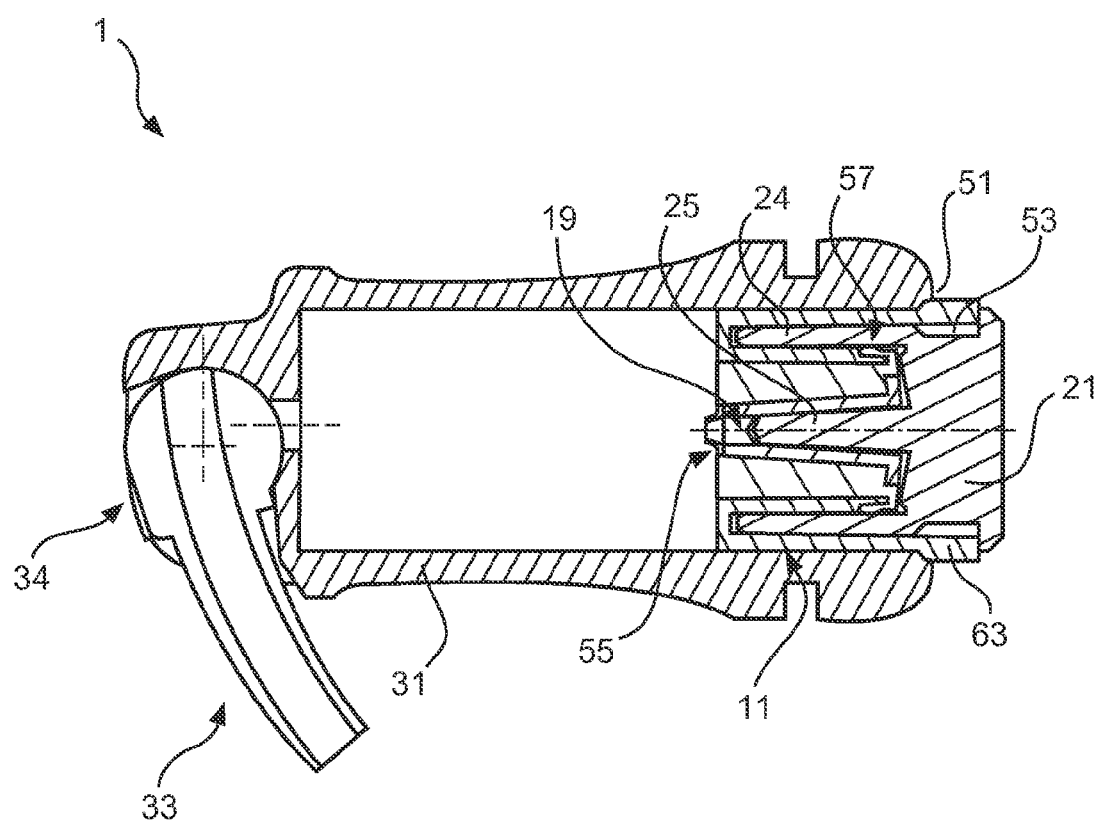
FIG. 3 is a cross-sectional view of the mixing and application capsule from FIG. 2 in a second operating position.
Figure 4:
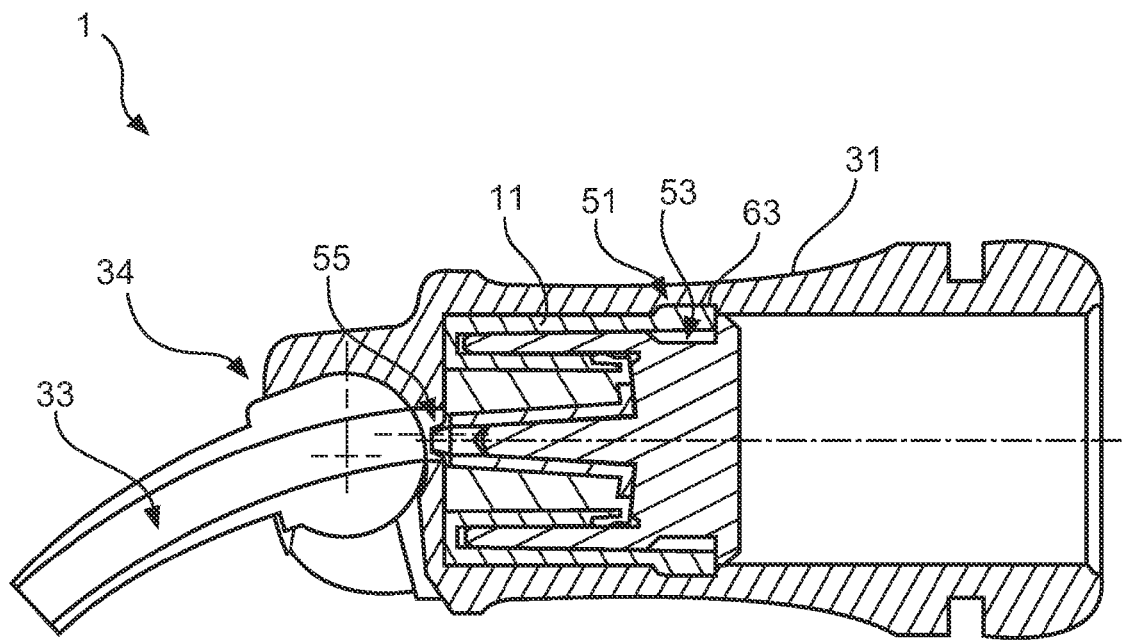
FIG. 4 is a cross-sectional view of the mixing and application capsule from FIGS. 1a-3 in a third operating position.

The operation of capsule 1 is explained in FIGS. 2-4.

FIG. 2 illustrates one embodiment of a mixing and application capsule for producing a dental preparation 43 with a capsule body 31, a first piston body 11 in the form of a punching piston and a second piston body 21 in the form of a liquid piston. The first piston body 11 consists of two different materials, namely a soft component and a hard component (fourth aspect of the invention). The capsule body 31 is of substantially cylindrical form and has, on a first end, a cannula 34, which is arranged rotatably by means of a hinged joint 35. The cannula-hinged joint arrangement 33, 35 is preferably designed as cannula-swivel element. In a first position (as shown in FIG. 2), the cap 34 and the cannula 33 are rotated by means of the hinged joint 35 in such a way that the interior of the cannula 33 is not connected to the mixing space 32 of the capsule body 31. In a second position, cap 34 and cannula 33 are arranged by means of the hinged joint 35 (as is explained below, referring to FIG. 2d) so that the dental paste 43 prepared inside the capsule body 31 can be expelled through the cannula 33.

Inside the capsule body 31, the mixing space 32 is arranged, which is in the form of a cavity and, in the filled state of the mixing and application capsule, has a pulverant component 41, which when mixed with liquid 42 forms the dental preparation 43. The mixing space 32 is delimited at the first end of the capsule body 31 by the cap-and-cannula arrangement 33, 34 and on the second, open end of the capsule body 31 by the punching piston 11. Furthermore, the component 41 can be not only pulverulent, but can also be in the form of paste, liquid or fluid.

The punching piston 11 is arranged movably along the longitudinal axis of the capsule body 31. It serves for expelling the dental paste 43 prepared in the mixing space 32 through the cannula 33. A fluid in the sense of this application is a substance that offers no resistance to an arbitrarily small shear stress, as applies in particular to gases and liquids. In the embodiment shown in FIGS. 1a and 1b, the channel 19 is formed along the central longitudinal axis of the punching piston 11. The channel 19 forms the connection between mixing space 32 and second piston body 21, which has a cavity 22 for receiving the fluid 42. The channel 19 is designed to prevent the pulverant component 42 passing into or through it into the channel.

The second piston body 21, in the form of a liquid piston, is arranged on the side of the first piston body 11 in the form of a punching piston turned away from the mixing space 32. The liquid piston 21 has a cavity 22 that is in particular sealable or sealably coated, in which the liquid 42 is arranged, which serves for mixing the dental preparation 43 in combination with the pulverant component 41. The cavity 22 of the liquid piston 21 is hermetically sealed by a separating layer 23.

The punching piston 11 has a projection 12 as a punch, which corresponds in form and/or volume to the cavity 22.

The cavity 22 of the liquid piston 21 is delimited laterally by a radial projection or edge projection 24, which forms the edge zone of the liquid piston 21 and the side wall of the cavity 22. The edge projection 24 serves for guidance of the liquid piston 21 during displacement along the longitudinal axis of the capsule body 31 and is received in a correspondingly formed edge recess 14 in the edge zone of the punching piston 11.

The capsule body 31 has a chamfer on its end on the piston body side. The first piston body 11 has a plurality of projections 63 with a corresponding chamfer 51. FIG. 2 shows the position of the first piston body with the chamfer 51 bearing on the corresponding chamfer of the capsule body 31. The second piston body 21 has an encircling recess 53, which is arranged proximally to the overhang 49.

Figure 5:
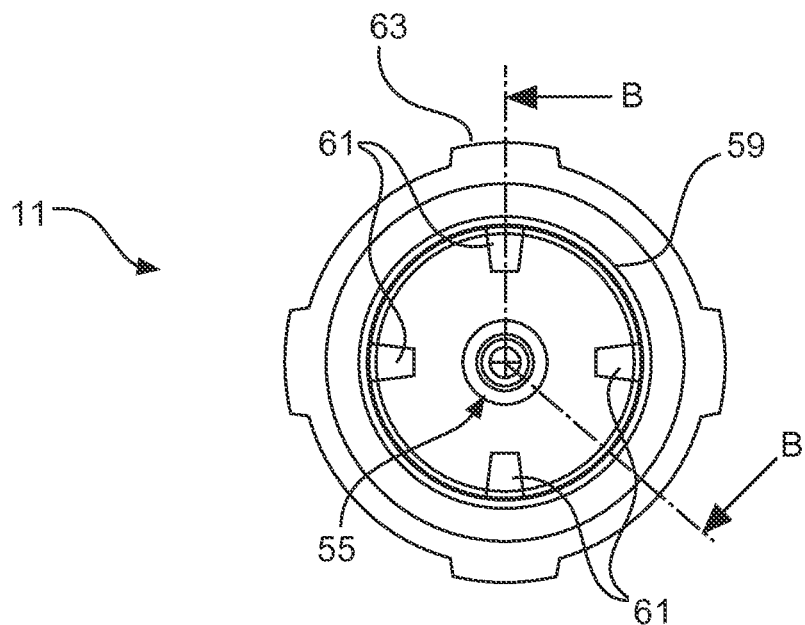
FIG. 5 is a detail view of a component of the mixing and application capsule according to the invention from FIGS. 1a-4.
Figure 6:
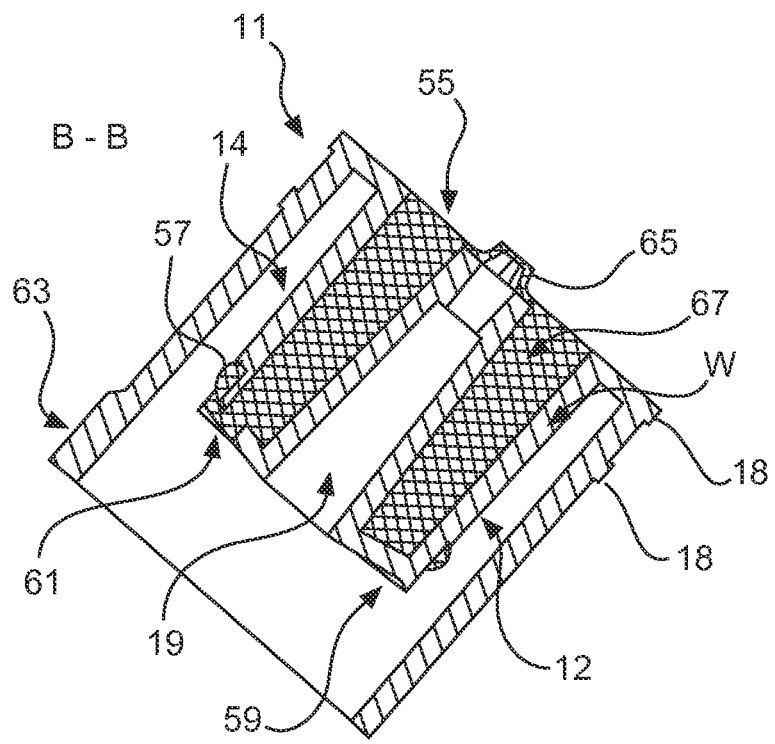
FIG. 6 is a cross-sectional view of the component shown in FIG. 5.
Figure 8:
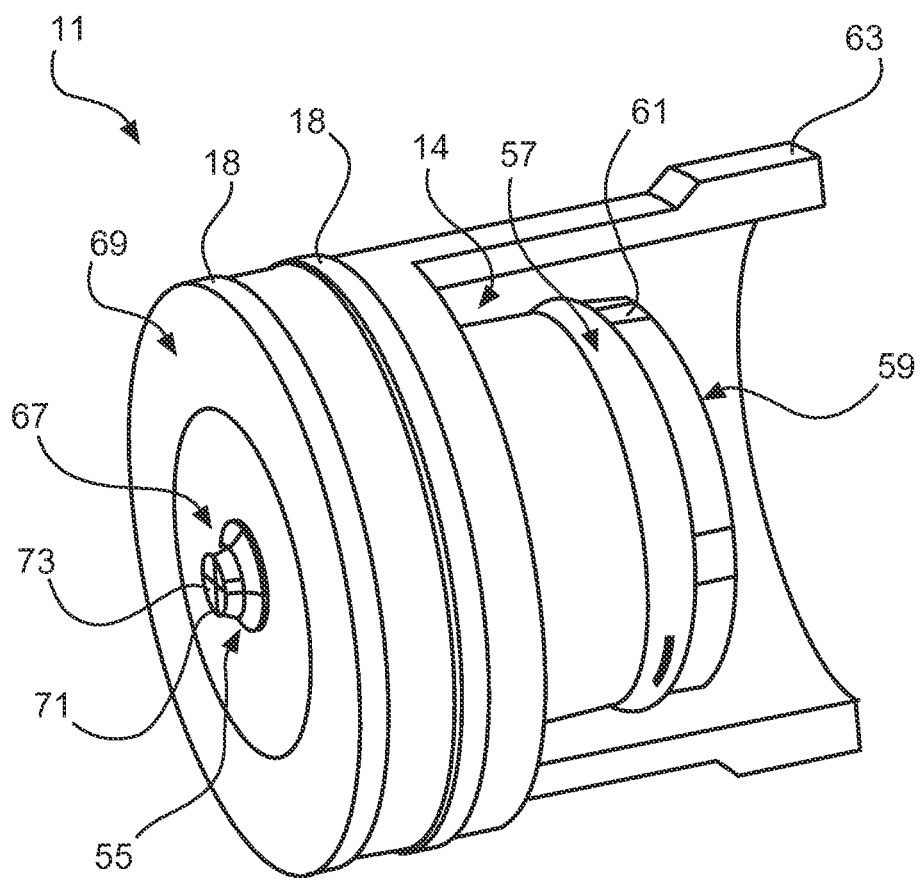

The first piston body 11 has, on an end of the channel 19 on the mixing space side, a closing means 55. Details of the closing means 55 are shown in FIGS. 5, 6 and 8. The first piston body 11 has a projection 12. The projection 12 has a ring seal 57 round its circumference. An edge recess 14 is formed between an outer wall of the first piston body 11 and the projection 12. The edge recess 14 is designed to receive a substantially annular edge projection 24 of the second piston body 21.

The operation of the mixing and application capsule according to the embodiment shown in FIG. 2 by activation and expulsion of the dental preparation is shown in FIGS. 2 through 4. The mixing and application capsule of FIGS. 2 through 4 has the capsule body 31, the punching piston 11 and the liquid piston 21. A liquid 42 is arranged in the cavity 22 of the liquid piston 21, the cavity 22 being sealed by a separating layer. The powder 41 is arranged in the mixing space 32 of the capsule body 31, which is delimited by the cap-and-cannula arrangement 33, 34 on the one hand and punching piston 11 on the other hand.

The operation of the mixing and application capsule according to the invention will now be explained, starting with FIG. 2. FIG. 2 shows the initial situation explained above. In a first step, pressure is exerted on the liquid piston 21 in the direction of the punching piston 11 along the longitudinal axis of the capsule body 31. By bringing the projection 12 of the punching piston 11 into contact with the separating layer 23 of the liquid piston 21, on further displacement of the liquid piston 21 the projection 12 cuts out a partial zone of the separating layer 23, wherein simultaneously the projection 25 pierces the separating layer 23, which is moreover deformed during the operation. The liquid cavity 22 is opened. The liquid 42 flows away directly through the channel 19 into the mixing space 32 of the capsule body 31.

Through further displacement of the liquid piston 21 towards the punching piston 11, the projection 12 of the punching piston 11 is introduced into the cavity 22 of the liquid piston 21, it displaces the liquid 42 from the cavity 22 and forces it into the channel 19 and the mixing space 32 of the capsule body 31. Because the liquid piston 21 is delimited laterally by the edge projection 24, which is introduced into the edge recess 14 of the punching piston 11, loss of liquid in the edge projection 24 and via the seal 57 between punching piston 11 and liquid piston is avoided. This is reinforced by the fact that the only possibility of escape for the air that is present in the edge recess 14 is through the channel 19, and this air entrains the liquid 42 with it. The air that is thus brought into the mixing space and the air that is displaced by the incoming liquid 42 escape through the venting devices of the first piston and/or the venting device of the capsule body.

In FIG. 3, the second piston body 21 has been inserted almost fully into the first piston body. The ring seal 57 is displaced by the preferably annular edge projection 24 of the second piston body 21 so far that the edge projection 24 on the ring seal 57 can extend beyond into the interior of the edge recess 14. The ring seal 57 provides a fluid-tight seal of the contact surface. In FIG. 3, the second piston body 21 is pushed into the first piston body 11 almost to the maximum, so that the overhang 49 bears on an end face of the first piston body 11. The projections 63, which mate with the corresponding chamfer of the capsule body 31, are—relative to the direction of insertion—brought axially into alignment with the encircling recess 53 of the second piston body 21. The projection 25 is received in the channel 19. The representation of the material overlap in FIG. 3 indicates, for simplicity of representation, on the one hand the surface pressure generated between the projection 25 and the channel 19, and on the other hand the formation of permanent flow channels in the regions where no surface pressure develops (third aspect of the invention).

If the projection 12 of the first piston body has been inserted fully into the cavity 22 of the second piston body, in which the liquid 42 was present in the initial situation, the first operation is completed. The amount of liquid provided for production is now in the mixing space 32 of the capsule body 31. Then mixing takes place in a mixer. These mixers are usual in dental practice and the capsule is subjected to a vigorous shaking motion, which is often directed substantially parallel to the longitudinal axis of the capsule. Therefore in most appliances the capsule is clamped in a holding fork and held in place by spring force. The clamping points are cap 34 and liquid piston 21. This has the effect that in each case in the reversing position of the shaking motion, as well as the spring force of the holding fork, additionally an accelerating force acts on the liquid piston 21 and possible incomplete emptying of liquid during mixing is further improved. Depending on the type of holding fork and mixer, it is moreover possible for activation to occur during clamping and/or during mixing. In this case manual activation is unnecessary.

The next operation for use of the mixing and application capsule serves for expulsion of the prepared paste 43 (FIG. 4). For this, the hinged joint 35 is brought into the second position, so that the cannula 33 forms a connection between mixing space 32 and outer zone of the mixing and application capsule. On exerting further pressure on the liquid piston 21, the liquid piston 21 and simultaneously the punching piston 11 are moved towards the mixing space 32 and its volume decreases. Simultaneously, the mixing space 32 is vented further by means of the venting device of the capsule body 31 or punching piston 11, if the air does not flow out of the cannula. The prepared paste 43 is expelled through the cannula 33 and can be applied.

For simplicity of representation, a material overlap between the projections 63 and the inside wall of the capsule body 31 is shown. In photorealistic representation, however, the respective projection 63 would, as a result of application of pressure of the second piston body, draw back at least partially into the encircling recess 53, so that displacement of the first piston body 11 inside the capsule body 31 becomes possible. In the position shown in FIG. 4, the first piston body 11 is in the state of maximum insertion in the capsule body 31, and the mixing space 32 is completely collapsed. The cannula 33 provides a fluid-conveying connection to the channel 19.

FIGS. 5-8 show in detail the first piston body 11 of the capsule 1 according to the first exemplary embodiment. It can be seen from FIG. 5 that the piston body 11 has a plurality of projections 63 along its outer circumferential surface. Four projections 63 are shown. The piston body 11 has a projection 12 (see FIG. 6), on the free end of which a cutting edge 59 is formed. The cutting edge 59 is arranged parting a separating layer 23 (see FIG. 2). The cutting edge 59 is formed in a plurality of regions 61, in the present case in four regions, consisting of soft component and therefore designed to consist intermittently of hard component and soft component. In FIG. 5, the view on the closing means 55 is opened.

FIG. 6 shows a cross-sectional projection along the cutting line B-B in FIG. 5. It can be seen that the piston body 11 has a structure W, which is formed substantially wave-shaped or corresponding to the letter W (second aspect of the invention). This structure W consists of hard component. The hard component in the wave-shaped region of structure W is formed with substantially constant wall thickness. In structure W, cavities are formed, which are filled with soft component 67.

The closing means 55 has a plurality of closing elements (first aspect of the invention), which are formed of soft component and are arranged on an end on the mixing space side of the channel 19. The closing elements support one another in the position shown.

The ring seal 57, which extends on the circumferential surface between the projection 12 and the edge recess 14, is formed of soft component and is formed integrally with those regions 61 of the cutting edge 59 that consist of soft component.

Figure 7:
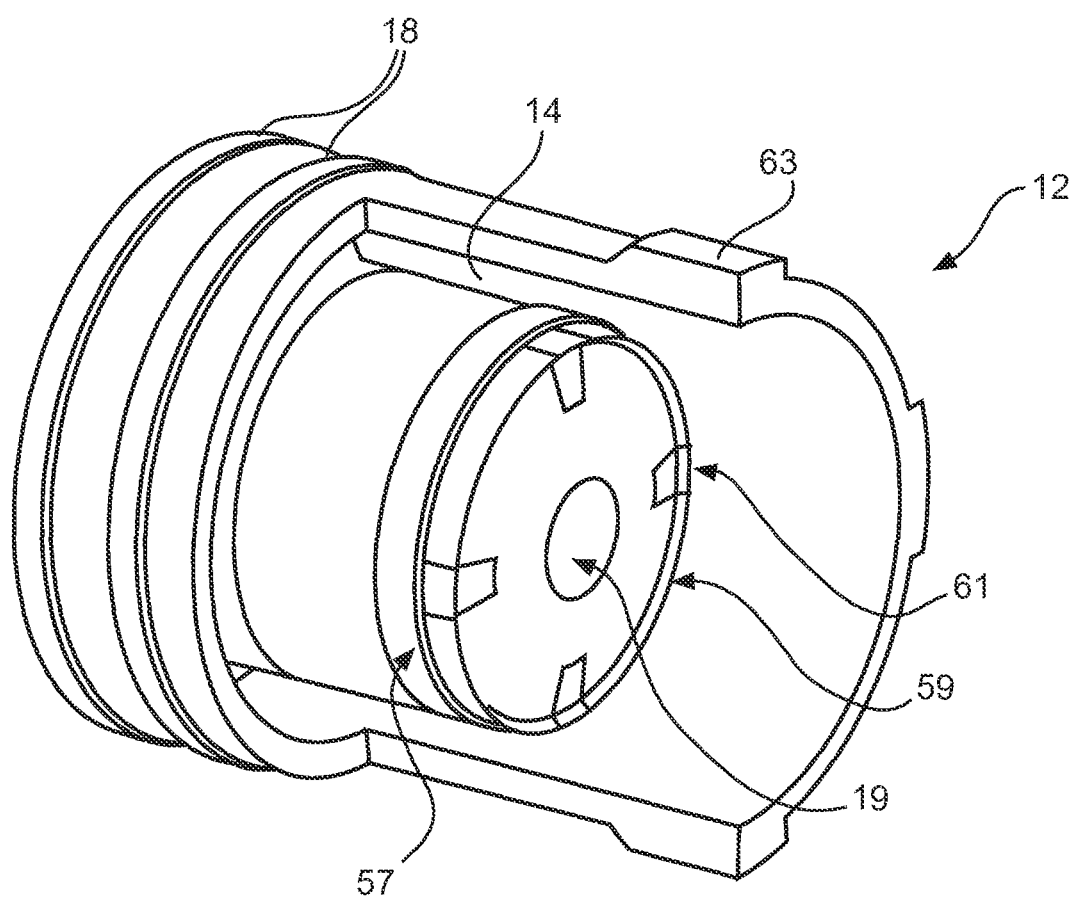
FIGS. 7, 8 is a three-dimensional representation of the component from FIGS. 5 and 6, FIGS. 9, 10 show cross-sectional views of a component of the mixing and application capsule according to the invention of a second exemplary embodiment according to the first through fourth aspect of the invention.

As is also shown in FIG. 7, the piston body 11 has, round its circumference, additionally to the projections 63, on an opposite end a plurality of, in the present case two, overhangs 18. The overhangs 18 serve for guidance of the piston body 11 within the capsule body 31 of the capsule 1 and sealing against escape of the prepared dental preparation in the application operation.

FIG. 8 shows a three-dimensional representation of the piston body 11. The closing means 55 is shown in detail (first aspect of the invention). The closing means 55 protrudes on the end face of the soft component 67 from an end face 69 of the piston body 11. A cross-shaped slit 71 is provided, which separates a total of four closing elements 73 from one another. The closing elements 73 are arranged so that, based on the example of a leaflet valve, on application of pressure from the interior of the channel 19 (see FIG. 7), they open outwards, to allow fluid transport towards the mixing space 32 (see FIGS. 2-4). The closing elements 73 support one another in the closed state, preventing transport of material in the opposite direction—that is, into the channel 19. The slit 71 is preferably made by means of a sharp blade or with laser radiation.

Figure 9:
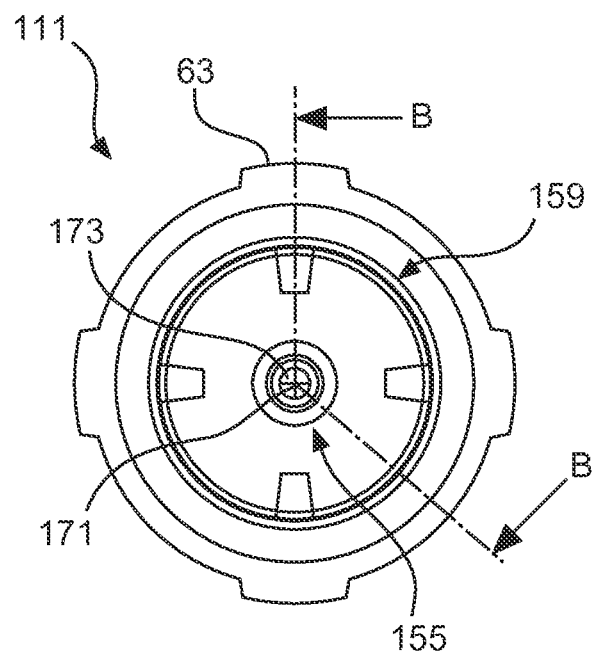
Figure 10:
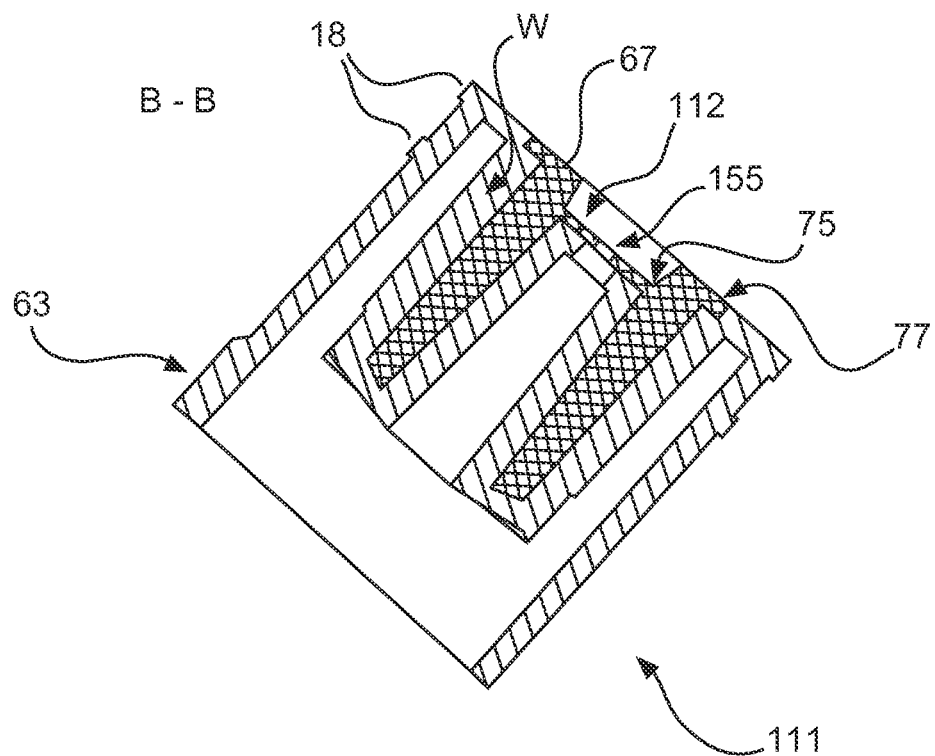

FIGS. 9 and 10 show a first piston body 111 for a capsule according to a second exemplary embodiment of the present invention. The piston body 111 is structurally similar to the piston body 11 from the first exemplary embodiment. Thus, the piston body 111 also has a total of four projections 63. In addition, the piston body 111 has two overhangs 18 on its outer circumference for guiding the piston body 111 within the capsule body 31 of the capsule 1. The piston body 111 also has a structure W with substantially constant wall thickness, which is formed from the hard component (second aspect of the invention), and has cavities, which are filled with the soft component 67. In contrast to the piston body 11 according to the first exemplary embodiment, the piston body 111 has a closing means 155 (first aspect of the invention). The closing means 155 is arranged in a depression 112 of the piston body 111 on the mixing space side. The closing means 155 has a total of four closing elements 173, which are separated from one another by a cross-shaped slit 171. The closing elements 173 are arranged substantially in one plane. The soft component 67 is joined to the hard component by welding, in accordance with the second exemplary embodiment. There is a first annular weld seam along the edge 75, and a second annular weld seam along the edge 77, as indicated in FIG. 10. Preferably ultrasonic or thermal welding is used. As a result of the encircling weld seam, the thick-walled cavity of the hard component is sealed hermetically against ingress of fluid during application of pressure (activation). With this method of joining, the desired function can also be achieved with combinations of materials that cannot be injection-molded by the two-component process. Alternatively, the soft component 67 and the hard component can be fastened to one another by gluing or injection molding. Injection molding is advantageous in particular for certain material combinations, as was discussed above in the description.

Figure 11:
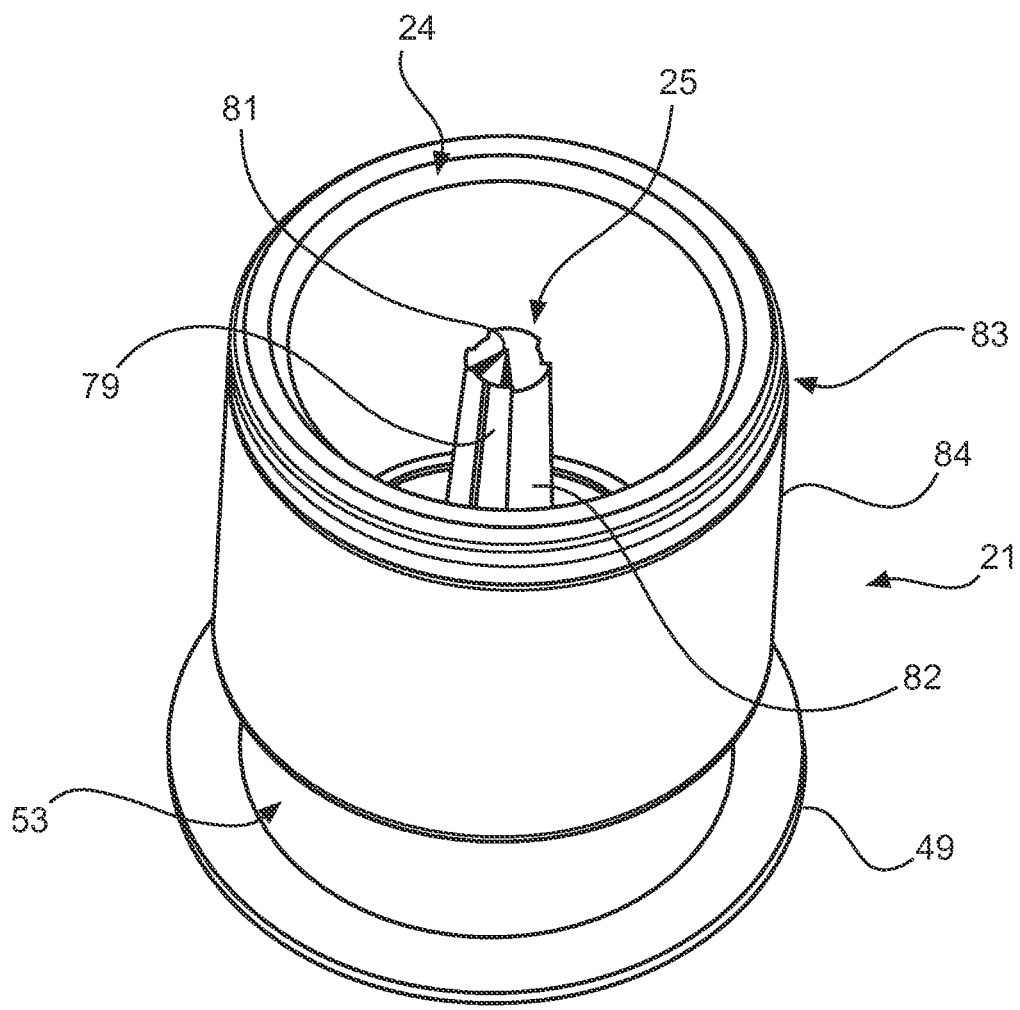
FIG. 11 is a three-dimensional representation of another component of the mixing and application capsule according to the invention according to both exemplary embodiments.

FIG. 11 shows a three-dimensional representation of a second piston body 21 of capsule 1 according to the invention. The second piston body 21, which has an encircling recess 53 and an overhang 49 (see also FIGS. 1, 2-4) and a projection 25, which according to FIG. 11 has a substantially conically tapering bearing surface 82. The projection 25 of the second piston body 21 is adapted to the channel 19 of the first piston body 11 (see FIGS. 2 through 10), so that with projection 25 and channel 19 bearing on one another, one or a plurality of flow channels remain (third aspect of the invention). The bearing surface 82 is interrupted by a total of three recesses 79. The recesses 79 extend in the longitudinal direction of the projection 25. A point 81 is formed on the tip of the projection 25. The point 81 facilitates the destruction of a separating layer (separating layer 23, see FIGS. 2-4).

A circumferential overhang 83 is formed along an outer circumferential surface 84 of the second piston body 21. The overhang 83 supports the guidance of the edge zone 24 of the second piston body 21 within the edge recess 14 of the first piston body (see FIGS. 2-4).

Figure 12:
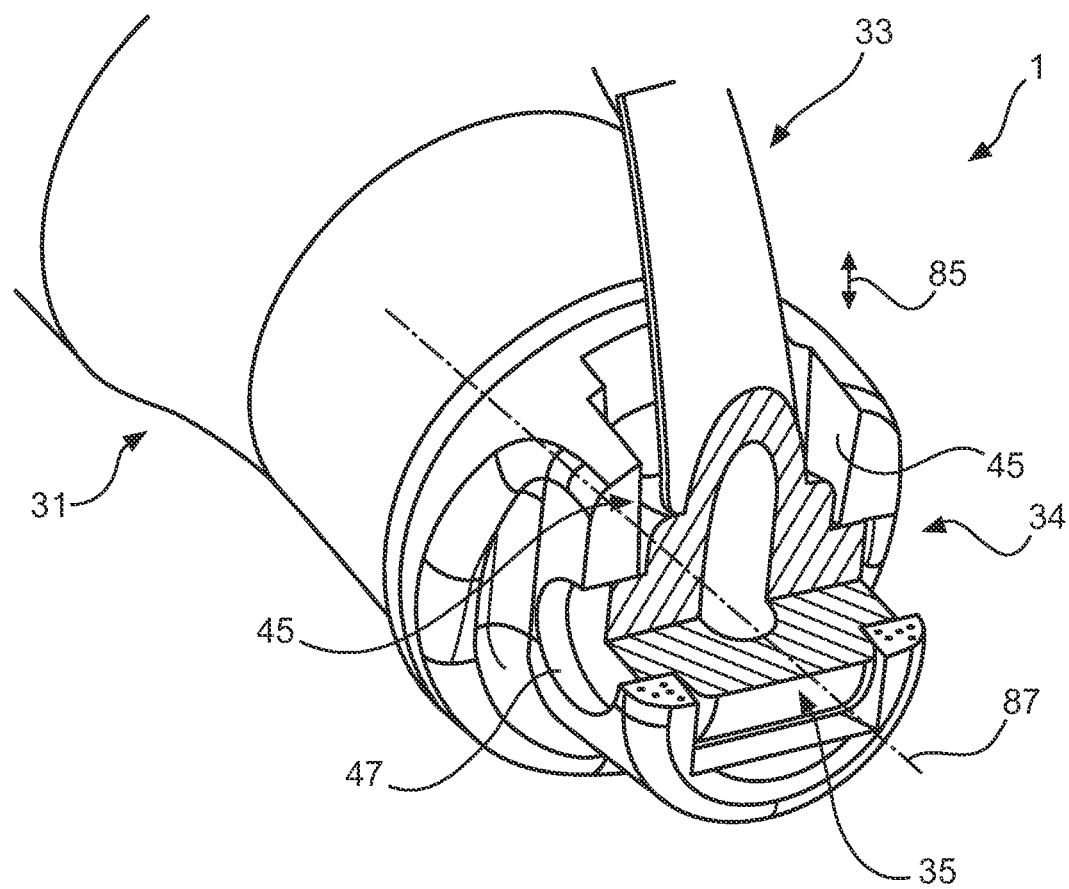
FIG. 12 is a detail view of the mixing and application capsule of the invention according to both exemplary embodiments.

FIG. 12 shows the end segment of capsule 1 on the cannula side. The cannula 33 is arranged on one end of the capsule body 31. The cannula 33 has a hinged joint 35, which is mounted rotatably in a seating 47. The cannula 33 is shown in the closed position in FIG. 12. The cannula 33 is inserted in the flanks 45 at an angle relative to the direction of expulsion (along axis 87) and is held in its snapped-in position. The direction of insertion and withdrawal of the cannula 33 is indicated by the arrows 85 in FIG. 12.

The invention claimed is:

1. A mixing and application capsule for producing a dental preparation, wherein the mixing and application capsule comprises:
 a capsule body with a mixing space for receiving a mixture component and for mixing the dental preparation from the mixture component and a fluid and with an outlet orifice for expelling the dental preparation,
 a first piston body that is longitudinally movable in the capsule body, and delimits the mixing space in the capsule body, said first piston body comprising a longitudinal channel, and
 a fluid cavity for receiving a fluid, wherein the fluid cavity and the mixing space are located at opposite ends of the longitudinal channel,
 wherein the first piston body comprises wholly or partly of two or a plurality of dissimilar materials, comprising at least one soft component and at least one hard component, wherein the first piston body comprises a first piston cavity, opening to a side proximate the mixing space,
 wherein said at least one soft component completely fills a radial gap of the first piston cavity between opposing surfaces of the at least one hard component and the at least one soft component wholly or partly comprises one or a plurality of closing elements covering a mixing space-side opening of said channel,
 wherein, at zero pressure, said closing elements abut to be impervious to passage of a mixture component into the channel, and wherein said closing elements are arranged so as to release fluid out of the channel in the direction of the mixing space on application of pressure on the fluid cavity.

2. The mixing and application capsule as claimed in claim 1, further comprising a mixture component in the mixing space,
 wherein the mixture component comprises a pulverulent material,
 wherein the pulverulent material has an average particle size ($d_{50}$) that is in a range from 1 μm through 100 μm; and/or
 wherein the mixture component is contained in the mixing space of the capsule body.

3. The mixing and application capsule as claimed in claim 1, wherein the closing elements are designed so that, on application of pressure, they release a slit-shaped, cross-shaped or star-shaped opening of the channel.

4. The mixing and application capsule as claimed in claim 1,
 further comprising a second piston body that is movable in the capsule body relative to the first piston body and has the cavity for receiving the fluid,
 wherein the first piston has a projection, and
 wherein the cavity of the second piston body is designed to receive the projection of the first piston body.

5. The mixing and application capsule as claimed in claim 1,
 wherein the first piston body has a projection,
 wherein a cavity of a second piston body is designed to receive a projection of the first piston body,
 wherein the projection is formed on the first piston body in such a way that the piston body has a structure (W) with substantially constant wall thickness, and wherein the structure (W) consists of the hard component.

6. The mixing and application capsule as claimed in claim 5,
 wherein one or a plurality of cavities are formed on the structure (W), which are filled wholly or partly with the soft component; and/or
 with the second piston body that is movable in the capsule body relative to the first piston body and has the cavity for receiving the fluid.

7. The mixing and application capsule as claimed in claim 5, wherein the second piston body is movable in the capsule body relative to the first piston body, and the cavity of the second piston body is adapted for holding the fluid and receiving a projection of the first piston,
 wherein the channel is designed to receive a projection of the second piston body, and wherein the projection of the second piston body and the channel are adapted to one another so that with the projection of the second piston body and the channel bearing on one another, one or a plurality of flow channels remain.

8. The mixing and application capsule as claimed in claim 7,
wherein the projection and the channel each have one or a plurality of bearing surfaces, which are sealed together fluid-tight with the projection and the channel bearing on one another.

9. The mixing and application capsule as claimed in claim 8,
wherein, in the one or a plurality of bearing surfaces of the projection, and/or in the one or the plurality of bearing surfaces of the channel, depressions are formed with walls that define one or a plurality of flow channels for fluid transport,
wherein the walls are deformable in such a way that the flow channels are wholly or partly sealable, on application of a pressing force on the projection in the bearing position and/or the channel.

10. The mixing and application capsule as claimed in claim 7,
wherein the first piston body has a projection, wherein the cavity, which is formed in the second piston body, is designed to receive the projection of the first piston body.

11. The mixing and application capsule as claimed in claim 7,
wherein the cavity is sealed by a separating layer, and wherein the projection of the first piston and/or the projection of the second piston are designed to penetrate the separating layer, when the first piston body and the second piston body are moved relative to one another; and/or
wherein the projection of the second piston body has, in sections or completely, a diameter that is greater than the diameter of the channel, so that when the projection is received in the channel, starting from a certain depth of penetration, the outside surface of the projection and the inside surface of the channel bear on one another at least partially fluid-tight; and/or
wherein the projection is of substantially conical form; and/or
wherein the channel has a cross-section that is enlarged, in the direction of the cavity; and/or
wherein the projection of the first piston body has a cutting edge for cutting into a separating layer, wherein the cutting edge is arranged along the periphery of the projection, and wherein a ring seal is arranged proximally to the cutting edge.

12. The mixing and application capsule as claimed in claim 7, wherein the mixing and application capsule comprises:
a second piston body that is movable in the capsule body relative to the first piston body, and has the cavity for receiving the fluid.

13. The mixing and application capsule as claimed in claim 7,
wherein the outlet orifice is arranged in a cannula, which is mounted rotatably on the end wall end of the capsule body,
wherein the cannula is fastened in a recess (A) on the capsule body, and
wherein the direction in which the cannula is snapped-in is angled to the direction of discharge of the dental preparation.

14. The mixing and application capsule as claimed in claim 7,
wherein the projection of the first piston body has a cutting edge for cutting into the separating layer, wherein the cutting edge is arranged along the periphery of the projection, and
the cutting edge consists intermittently of the soft component and of the hard component along the circumference; and/or
wherein the second piston body has an overhang, on an end opposite the cavity; and/or
wherein the material of the soft component comprises a thermoplastic elastomer (TPE) and the material of the hard component comprises polypropylene, and/or
wherein the material of the soft component comprises silicone and the material of the hard component comprises a polyester; and/or
wherein the material of the soft component comprises a thermoplastic elastomer (TPE) and the material of the hard component comprises polyoxymethylene (POM), and/or
wherein the material of the soft component comprises polyethylene (PE) and the material of the hard component comprises polypropylene (PP), and/or
wherein the second piston body comprises of high-density polyethylene (HDPE) and the separating layer comprises of polyethylene (PE).

15. The mixing and application capsule as claimed in claim 14, wherein the soft component comprises four regions that are spaced angularly apart by 90°.

* * * * *